United States Patent [19]

Perlberger

[11] 4,418,020

[45] Nov. 29, 1983

[54] 2,2-DICHLOROACETOACETYL CHLORIDE

[75] Inventor: Jean-Claude Perlberger, Miege, Switzerland

[73] Assignee: Lonza Ltd., Basel, Switzerland

[21] Appl. No.: 321,053

[22] Filed: Nov. 13, 1981

[30] Foreign Application Priority Data

Nov. 19, 1980 [CH] Switzerland .................. 8549/80

[51] Int. Cl.³ .............................................. C07C 53/50
[52] U.S. Cl. ............................................. 260/544 Y
[58] Field of Search ................................. 260/544 Y

[56] References Cited

U.S. PATENT DOCUMENTS 3,576,860  4/1971  Zazaris ........................... 260/544 Y
3,700,053  10/1972  Pawloski et al. .................. 568/407
3,701,803  10/1972  Boosen ........................... 260/544 Y

OTHER PUBLICATIONS

Beilstein, "Handbuch der Organischen Chemie", vol. 3 (1922) p. 634.
Jolly, William L., The Synthesis and Characterization of Inorganic Compounds, (1971) Prentice-Hall, Inc., p. 50.
Journal of the Chemical Society, London, 1928, pp. 2779-2786.

Primary Examiner—Natalie Trousof
Assistant Examiner—L. Hendriksen
Attorney, Agent, or Firm—Fisher, Christen & Sabol

[57] ABSTRACT

2,2-Dichloroacetoacetyl chloride having the formula:

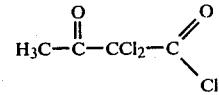

Process for producing 2,2-dichloroacetoacetyl chloride wherein acetyl chloride is reacted by means of a Lewis acid as a catalyst with chlorine at a temperature of 30° to 60° C. The mole ratio of acetyl chloride to the catalyst is from 1:0.005 to 1:0.5 and the mole ratio of acetyl chloride to the chlorine is from 1:0.1 to 1:1.5. The most preferred catalysts are aluminum chloride and aluminum bromide.

1 Claim, No Drawings

2,2-DICHLOROACETOACETYL CHLORIDE

BACKGROUND OF THIS INVENTION

1. Field of This Invention

This invention is concerned with 2,2-dichloroacetoacetyl chloride and a procedure for producing it.

2. Prior Art

It is known that the chlorination of acetyl chloride with chlorine provides chloroacetyl chloride as a main product and dichloroacetyl chloride as a by-product. In fact, without the use of catalysts such a reaction only proceeds very slowly. Known catalysts, such as, iodine [H. B. Watson and E. E. Roberts, J. Chem. Soc., 2779, (1928)], sulfuric acid (German O. S. 22 63 580) and chlorosulfonic acid (German O. S. 27 29 911), for such reaction permit a suppression of the formation of dichloroacetyl chloride, but do not promote the formation of 2,2-dichloroacetoacetyl chloride, and do particularly favor the formation of chloroalkanoyl chloride.

BROAD DESCRIPTION OF THIS INVENTION

An object of this invention is to provide 2,2-dichloroacetoacetyl chloride. Another object of this present invention is to provide a technically simple procedure for producing the compound 2,2-dichloroacetoacetyl chloride in which the formation of by-products, such as, chloracetyl chloride and dichloracetyl chloride is avoided in the main and to the extent possible. Other objects and advantages of this invention are set out herein or are obvious herefrom to one ordinarily skilled in the art.

The objects and advantages of this invention are provided by the process and compound of this invention.

In accordance with this invention, the production of 2,2-dichloroacetoacetyl chloride is achieved by having the chlorination of acetyl chloride with chlorine take place in the presence of a Lewis acid as a catalyst. Inorganic Lewis acids, particularly aluminum halides, and preferably aluminum chloride AlCl$_3$ and aluminum bromide AlBr$_3$, are quite advantageous. In order to obtain an optimum yield, it is necessary to permit the reaction to take place at a temperature of 30° to 60° C., and preferably from 40° to 50° C., with the mole ratio between acetyl chloride and the catalyst, and acetyl chloride and the chlorine (which are being fed in) being from 1:0.005 to 1:0.5 and from 1:0.1 to 1:1.5, respectively, and preferably 1:0.03 to 1:1.02 for both.

When carrying out the chlorination of acetyl chloride with chlorine in the presence of a Lewis acid, preferably of AlCl$_3$ or AlBr$_3$, as a catalyst, the expected chloracetyl chloride and dichloroacetyl chloride are not the chief products—but surprisingly the new compound 2,2-dichloroacetoacetyl chloride (not described in the literature) is produced and isolated in great excess and at a good yield.

A Lewis acid is a substance that accepts an electron pair. Examples of inorganic Lewis acids are BF$_3$, SnCl$_4$, AlCl$_3$ and AlBr$_3$.

This invention also includes 2,2-dichloroacetoacetyl chloride, which has the formula:

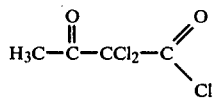

2,2-Dichloroacetoacetyl chloride is a new raw material for the specific manufacture of 2,2-dichloroacetoacetic acid and its esters and amides and of 1,1-dichloro acetone, which are particularly used in preparing insecticides.

By way of summary, 2,2-dichloroacetoacetyl chloride can be produced by chlorinating acetyl chloride with chlorine in the presence of Lewis acid, as a catalyst, at 30° to 60° C. with the mole ratio of acetyl chloride to the catalyst being from 1:0.005 to 1:0.5 and the mole ratio of acetyl chloride to the chlorine being 1:0.1 to 1:1.5.

DETAILED DESCRIPTION OF THIS INVENTION

As used herein, all percentages, ratios and proportions are on a weight basis unless otherwise stated herein or obvious herefrom to one ordinarily skilled in the art.

EXAMPLE 1

39.25 g (0.5 mole) of acetyl chloride and 2 g (0.015 mole) of aluminum chloride were put into a round bottom flask provided with a return-flow cooler (dry ice, acetone), a thermometer, a magnetic stirrer and a feed tube. The mixture was heated to 45° C. and then 36 g (0.51 mole) of chlorine was introduced at that temperature over a 2.5 hour period. The hydrochloric acid which was formed was absorbed in water and titrated (17.6 g; 0.48 mole).

The GC analysis of the reaction mixture (46.8 g) gave the following results:
14.3 percent of acetyl chloride
12.0 percent of chloroacetyl chloride (CAC)
1.5 percent dichloroacetyl chloride (DCAC)
7.0 percent of trichloroacetyl chloride
61.7 percent of 2,2-dichloroacetoacetyl chloride (DCAAC). This corresponds to a yield of 60.6 percent with a selectivity of 73 percent.

The reprocessing of the 2,2-dichloroacetoacetyl chloride and its separation from the reaction mixture were accomplished by distillation, first at normal pressure and then at 100 Torr (95° to 97° C.). The corresponding fraction contained the desired 2,2-dichloroacetoacetyl chloride at a purity of 98.7 percent.

EXAMPLES 2 TO 5

Examples 2 to 5 were carried out in the same way and using the same proportions as in Example 1. Example 5, which uses iodine, was a contrasting or comparison example. The conditions and results are given in the following table.

TABLE

| Example | Catalyst | Acetyl Chloride (AC) turnover, percent | Selectivity, percent | | | Yield of DCAAC in percent calculated from AC used |
|---|---|---|---|---|---|---|
| | | | CAC | DCAC | DCAAC | |
| 2 | AlCl$_3$ | 83 | 12 | 1.2 | 73 | 60.6 |
| 3 | AlBr$_3$ | 94.5 | 10 | 0.4 | 73 | 69.0 |
| 4 | SbCl$_3$ | 88 | 39 | 3.5 | 31 | 27.3 |
| 5 | iodine | 38 | 99 | 1.0 | 0 | 0 |

What is claimed is:

1. 2,2-Dichloroacetoacetyl chloride having the formula:

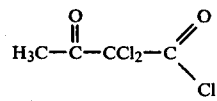

* * * * *